United States Patent
Ott (10) Patent No.: US 6,733,479 B1
(45) Date of Patent: May 11, 2004

(54) PERFORATED TROCAR SLEEVE AND METHOD OF USE

(76) Inventor: Douglas E. Ott, 682 Foster Rd., Macon, GA (US) 31210

( * ) Notice: Subject to any disclaimer, the term of this patent is extended or adjusted under 35 U.S.C. 154(b) by 0 days.

(21) Appl. No.: 09/627,971

(22) Filed: Jul. 28, 2000

Related U.S. Application Data (60) Provisional application No. 60/146,633, filed on Jul. 30, 1999.

(51) Int. Cl.$^7$ ............................................. A61M 25/00
(52) U.S. Cl. ................... 604/264; 604/158; 604/166.01
(58) Field of Search ................................ 604/158, 160, 604/164.02, 164.03, 164.09, 164.1, 166.01, 170.02, 264

(56) References Cited

U.S. PATENT DOCUMENTS

| | | |
|---|---|---|
| 2,711,740 A | 6/1955 | Pickens |
| 3,810,471 A | 5/1974 | Truhan |
| 3,982,533 A | 9/1976 | Wiest ................. 128/184 |
| 4,071,027 A | 1/1978 | Meador |
| 4,141,360 A | 2/1979 | Lasswell |
| 4,487,600 A | 12/1984 | Brownlie et al. |
| 4,535,773 A | 8/1985 | Yoon |
| 4,950,232 A | 8/1990 | Ruzicka et al. |

(List continued on next page.)

FOREIGN PATENT DOCUMENTS

| | | |
|---|---|---|
| EP | 0 399 712 | 5/1989 |
| WO | WO 93/08864 | 5/1993 |
| WO | WO 96/01132 | 1/1996 |

OTHER PUBLICATIONS

*Principle Cannulas, Trocars, and Telescopes,* by Gomel et al.; Laparoscopy and Hysteroscopy in Gynecologic Practice, pp 15–16.
*Severe Local Hypothermia from Laparoscopic Gas Evaporative Jet Cooling: A Mechanism to Explain Clinical Observations,* by Gray et al.; Mercer University; Department of Biomedical Engineering.
*Operative Gynecologic Laparoscopy Principles and Techniques,* by Camran R. Nezhat, M.D. et al.; pp 80–88.
*Textbook of Laparoscopy,* by Jaroslav F. Hulka, M.D. et al.; Second Edition; pp 66, 87–95, 99–100, 168.
*Surgical Laparoscopy,* by Karl A. Zucker, M.D. et al; 1991; pp 40–41, 87–90.
*Operative Manual for Endoscopic Abdominal Surgery, Operative Pelviscopy, Operative Laparoscopy,* by o. Prof. Dr. med. Dr. Med. Vet. H. c. K. SEMM; p 146.
*Performing a Safe Laparoscopy,* by Phillippe J. Quilici, M.D.; Laparoscopic Technical Manual; www.Laparoscopy.net/pesafe.htm; Jul. 20, 2000; pp. 1–5; *Performing a Safe Laparoscopy II,* www.Laparoscopy.net/pesafe2.htm; Jul. 20, 2000, pp. 1–5.
*Trocar,* Surgeon's Reference for Minimally Invasive Surgery Products; ISBN 1–56363–073–7; 1994; pp 157–172.

*Primary Examiner*—Thomas Denion
*Assistant Examiner*—Jaime Corrigan
(74) *Attorney, Agent, or Firm*—Jacobson & Johnson (57) ABSTRACT

A perforated trocar sleeve (20) is disclosed. The trocar sleeve has an elongate tubular body member (21) having a proximal end (22) and a spaced distal end (24). An inlet port (25) is defined in the proximal end of the body member, and an outlet port (26) is defined at the distal end thereof. The inlet and outlet ports, in association with the body member, define a continuous fluid flow conduit (28) within the body member. A plurality of openings (29) are defined in the exterior surface of the tubular body member and extend from the distal end of the body member at least partially toward the proximal end thereof. The fluid to be delivered into a body cavity is passed through these openings and dispersed through an arc extending radially about the axis of the body member. The openings may be spaced randomly or regularly along the length of the body member, and may be positioned within at least one recess (40,60) defined within the exterior surface of the body member. The openings defined in the body member may vary in size along the length of the body member.

26 Claims, 7 Drawing Sheets

U.S. PATENT DOCUMENTS

| | | |
|---|---|---|
| 5,104,381 A | 4/1992 | Gresl et al. .................. 604/164 |
| 5,186,714 A | 2/1993 | Boudreault et al. |
| 5,199,944 A | 4/1993 | Cosmescu .................... 604/26 |
| 5,217,468 A | 6/1993 | Clement |
| 5,334,159 A | 8/1994 | Turkel |
| 5,536,242 A | 7/1996 | Willard et al. |
| 5,605,537 A | 2/1997 | Ivey |
| 5,618,296 A | 4/1997 | Sorensen et al. |
| 5,637,096 A * | 6/1997 | Yoon .......................... 604/158 |
| 5,662,673 A | 9/1997 | Kieturakis .................. 606/185 |
| 5,800,409 A | 9/1998 | Bruce .......................... 604/280 |
| 5,882,345 A * | 3/1999 | Yoon .......................... 604/104 |
| 5,931,831 A | 8/1999 | Linder ........................ 604/523 |
| 6,063,099 A * | 5/2000 | Danks et al. ............... 604/264 |
| 6,228,068 B1 * | 5/2001 | Yoon .......................... 604/105 |

* cited by examiner

PERFORATED TROCAR SLEEVE AND METHOD OF USE

CROSS REFERENCE TO RELATED APPLICATION

This application claims priority to U.S. patent application Ser. No. 60/146,633, filed Jul. 30, 1999, in the United States Patent and Trademark Office, and the benefit of the filing date thereof.

FIELD OF THE INVENTION

The present invention relates to the field of medical instruments. More particularly, the present invention relates to an improved trocar sleeve, and the manner in which a pressurized fluid may be dispersed through the trocar sleeve.

BACKGROUND OF THE INVENTION

During the performance of certain surgical procedures a surgeon may need to use a needle or a trocar device to deliver fluid into a body cavity, or a portion of a body, for the purposes of inflating or distending the body cavity to make it easier to see and perform the desired treatment. Common procedures in which insufflation is used include any type of an endoscopic surgical procedure, as well as laparoscopic or thoracoscopic surgical procedures performed in the abdominal or thoracic body cavities, respectively. In these procedures a blind incision, for example, or a Verres needle may be used to initially traverse the skin and tissue layers until the body cavity is entered for the purpose of passing a pressurized fluid, either a gas or a liquid, into the body cavity.

If a Verres needle has been used penetrated into the body cavity, an external gas source is attached to a proximal end of the needle projecting outwardly of the body cavity. Under pressure, the desired fluid flows from the proximal end of the needle to a distal end thereof from which the fluid exits and is delivered into the body cavity for inflating the body cavity. When a blind incision is made, a standard trocar assembly may then be passed through the incision and into the body cavity, whereupon the desired fluid is passed through the trocar into the body cavity. In either instance, this process is known as insufflation, in which the desired fluid, as well as any other substances, which may include drugs and anesthetics, is passed under pressure into the body cavity. A commonly used gas for this procedure is carbon dioxide. Depending on the patient's size, medical condition, the procedure to be performed, and the surgeon's preference, the gas is flowed into the body cavity at a rate of from 0.1 to 20 liters per minute.

As described, in addition to Verres needles, physicians also use trocars, or trocar assemblies for the purposes of passing a pressurized fluid within a body cavity. The known trocar assemblies have a solid outer sheath or sleeve sized and shaped to be passed through the incision and tissue layers of a body so that the sleeve penetrates at least partially into the body cavity. This is accomplished by passing an elongate central retracting piercing element, referred to as a trocar or an obturator, through the sleeve and then passing the sleeve and the trocar together through the tissue. Once the sleeve is passed into the body cavity to the desired depth, the trocar is withdrawn from the sleeve.

During the insufflation process the gas distends the body cavity to move the tissue layers outwardly of the body to create sufficient space in the cavity to observe or treat the organs and/or body structures therein, and to also move the distal end of the trocar or Verres needle therefrom. Once the body cavity is distended with gas and the obturator of the trocar is withdrawn from the lumen of the trocar sleeve, viewing and surgical instruments are typically passed therethrough, while fluid may be continuing to flow therethrough as well, in order to allow the surgeon to visualize the contents of the body cavity and proceed with the desired diagnostic and/or surgical procedures without damaging the remaining tissues, organs, or body structures within the body cavity.

Figure 1A:
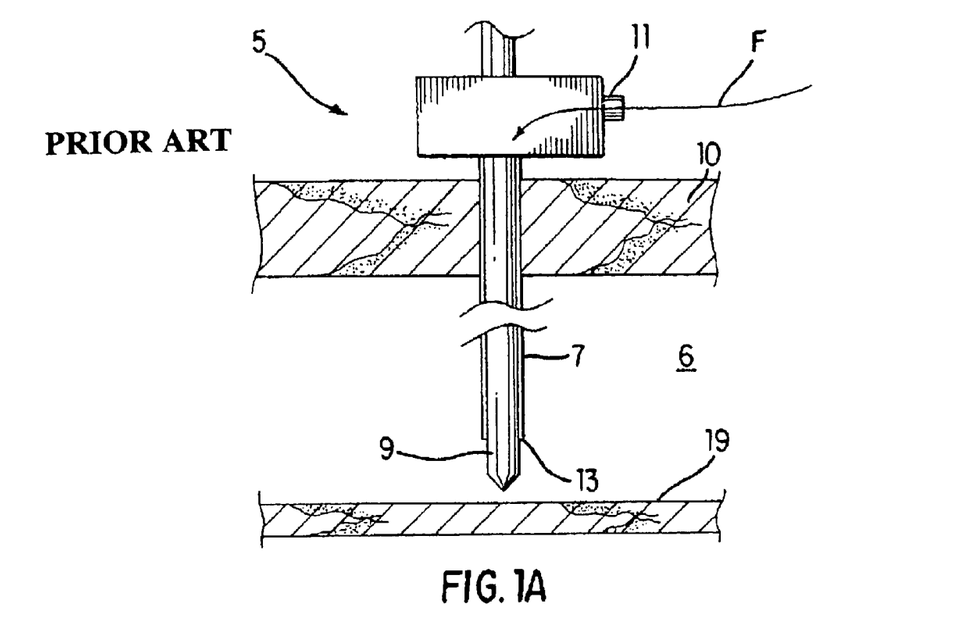
FIGS. 1A and B are schematic illustrations of a known type of trocar sleeve.
Figure 1B:
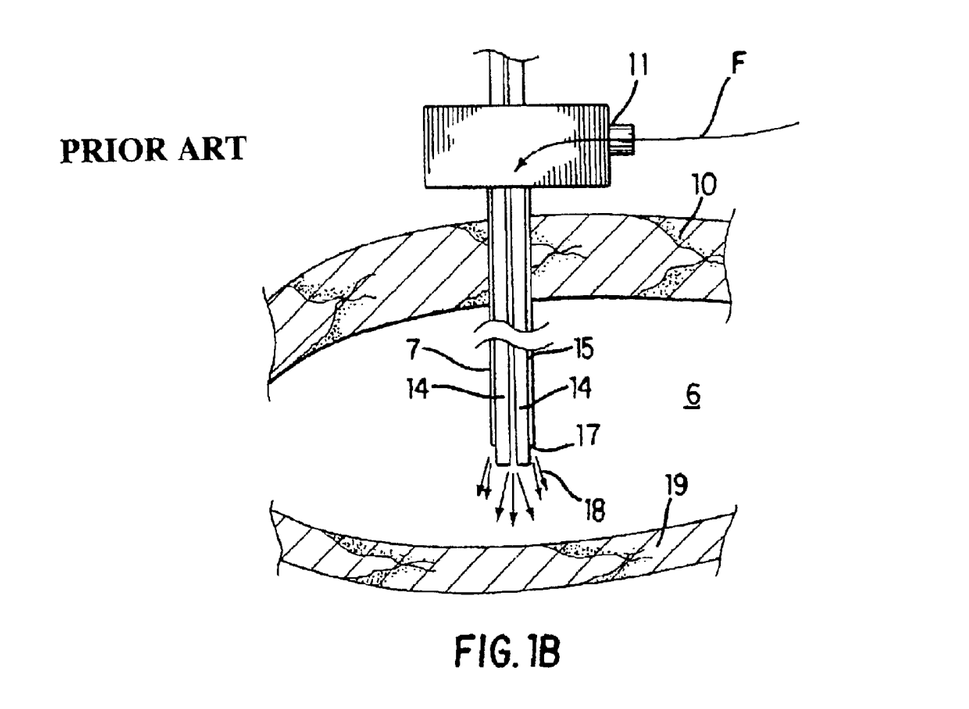

An example of the known types of trocar assemblies is illustrated in FIGS. 1A and B, in which a trocar assembly 5 is shown being used to gain access to a body cavity 6. The trocar assembly is comprised of a solid outer sheath or sleeve 7 containing within its lumen the trocar 9, the removable piercing element. The trocar is used together with the trocar sleeve to pierce the skin, the subcutaneous tissue, the fascia, the muscle, and the innermost layer of the cavity, collectively referred to as 10, to include the parietal peritoneum or the pleura, respectively, for either the abdominal or chest cavities.

As the trocar is being inserted into the body cavity, a fluid "F" from an external source, which may be a gas or a liquid bearing drugs, anesthetics, or other substances placed or mixed within a pharmaceutically acceptable carrier, or any combination thereof, is commonly passed through the access port 11 and transported into the body cavity through the distal end 13 of the trocar sleeve. It is commonplace in procedures of this type that the fluid F will also continue to be passed into the body cavity once the trocar is removed. The access port extends from the proximal end of the trocar sleeve exposed above the skin of the patient. As shown in FIG. 1B, various instruments 14, to include light sources, viewing scopes, graspers, manipulators, irrigators, suction devices, sutures, lasers, coagulators, biopsy devices, clip appliers and needle holders, may be placed through the lumen of the trocar sleeve and into the body cavity for the treatment or procedure to be performed.

Because the trocar sleeve will typically have at least one surgical instrument and/or a viewing device placed within its lumen, the cross-sectional area 15 of the unobstructed lumen available for fluid flow is markedly reduced. The fluid is forced to flow between the outer surface of the instrument(s) within the lumen and the internal surface of the trocar sleeve, which restricts the amount of fluid that may be passed through the trocar sleeve and into the body cavity through a relatively small opening 17 in the distal end of the trocar sleeve. Depending on the flow rate of the fluid at the entrance to the trocar sleeve, and the diameter of the sleeve and the restriction(s) within the sleeve reducing the effective fluid transport diameter, the stream of fluid passed from the distal end of the trocar can be quite forceful and is oftentimes formed into a "jet" stream 18 of a highly concentrated flow rate at a relatively high fluid velocity. This in turn defines an impact site for the tissues/organs impinged by the jetted fluid, and also limits the dispersion of the agents contained within the fluid stream within the body cavity.

The problem this jet streaming causes is that the jet streamed fluid may cause severe local heat loss from the lining of the body cavity 19 (FIG. 1A) and the surfaces of the organs housed therein as the fluid contacts those tissue surfaces. This phenomena is discussed in greater detail in the paper entitled *"Severe Local Hypothermia From Laparoscopic Gas Evaporative Jet Cooling: A Mechanism To Explain Clinical Observations,"* authored by R. I. Gray, D. Ott, A. C. Henderson, S. A. Cochran, and E. A. Roth, in the Journal Of The Society Of Laparoendoscopic Surgeons for August, 1999.

Because of these problems associated with the known types of trocar assemblies and sleeves, namely the postoperative hypothermia and suboptimal dispersion of therapeutic agents within the body cavity resulting from this jet streaming, there exists a great need for a trocar sleeve that will minimize or eliminate these jet streaming effects, to include limiting the possibility of damaging tissues and organs within the body cavity while efficiently dispersing the desired fluids through the trocar sleeve and into the body cavity at reduced fluid pressures.

SUMMARY OF THE INVENTION

The present invention provides an improved trocar sleeve adapted to minimize the likelihood of forming a jetstream of the fluid being passed through the sleeve and into a body cavity, and which will more efficiently disperse the fluids in the body cavity. The trocar sleeve of this invention provides a simple and efficient device, system, and method for efficiently and safely passing a fluid into a body cavity during a surgical procedure. Moreover, the relative simplicity of the improved trocar sleeve of this invention addresses the problems of efficiently and effectively introducing fluids into a body cavity during the performance of a surgical procedure requiring the insulation of a body cavity.

The invention provides an improved trocar sleeve for insertion into a body for use in delivering a pressurized fluid stream carrying one or more agents under pressure into the body. The device includes an elongate tubular body member formed about a longitudinal axis, having a proximal end and a spaced distal end. An inlet port is defined at the proximal end of the body member, and an outlet port is defined at the distal end thereof. Together the inlet port and the outlet port, in cooperation with the body member, define a fluid conduit extending substantially the length of the body member. A plurality of spaced openings are defined in the body member and open into the conduit, the openings extending from the distal end of the body member at least partially toward the proximal end thereof. The fluid to be delivered into the body is passed through the body member and dispersed through these openings in an arc extending radially about the axis of the body member.

The plurality of spaced openings defined in the body member may be randomly spaced, or regularly spaced, as desired. In one embodiment, a series of recessed dimples is formed in the exterior surface of the trocar sleeve, the plurality of spaced openings being defined within separate ones of these dimples. In another embodiment, a continuous helical groove is defined within the exterior surface of the body member extending from the distal end thereof at least partially toward the proximal end of the body member, and within which the openings are defined.

As described, the fluid is passed through the openings defined in the trocar sleeve and into a radial arc about the body member, which arc may be of any desired degree. This may include, therefore, an arc of approximately one hundred eighty degrees, or an arc of three hundred sixty degrees, as desired.

The openings defined in the trocar sleeve are in the range of from 0.01 millimeter to approximately 5 millimeters in diameter. These openings may vary in size as they extend along the length of the body member, either increasing or decreasing in size as they extend from the distal end toward the proximal end of the body member.

The openings defined within the exterior surface of the trocar sleeve may be shaped to be circular, elongate, or of any desired shape. Where elongate, the openings may be formed parallel to the axis of the body member, perpendicular thereto, or parallel to one another and aligned at an angle with respect to the axis of the body member.

The device may further include an elongate tubular inner sheath constructed and arranged to slide within the conduit of the body member, and at least partially along the length thereof. The tubular inner sheath is used to selectively open and close selected ones of the plurality of openings defined within the trocar sleeve.

The improved trocar sleeve of this invention also results in a novel system for reducing the pressure of, and also radially dispersing, a delivered pressurized fluid stream carrying one or more agents into a body. The system comprises the above-described trocar sleeve, a pressurized supply of the fluid to be passed into the body through the sleeve, and a device for introducing the fluid into the body member of the trocar sleeve.

Similarly, a unique method of delivering a pressurized fluid stream carrying one or more agents under pressure to a body also results from this invention. This method includes the steps of inserting a distal end of a tubular body member into the body, passing the fluid to be delivered into a proximal end of the trocar sleeve, and dispersing the fluid from the trocar sleeve and into the body through a plurality of spaced openings defined in the trocar, the plurality of openings extending from a distal end of the body member at least partially toward the proximal end thereof, through an arc extending radially about the axis of the body member.

It is to these objects, as well as the other objects, features, and advantages of the present invention, which will become apparent upon reading the specification and when taken in conjunction with the accompanying drawings, to which the invention is directed.

BRIEF DESCRIPTIONS OF THE DRAWINGS

FIGS. 8 A and B are top plan views of illustrative radial dispersion patterns of the fluids passed through the trocar sleeve of this invention.

FIGS. 10 A through C illustrate alternate embodiments of the fluid dispersal openings defined within a trocar sleeve of this invention.

DETAILED DESCRIPTION OF THE INVENTION

Figure 2:
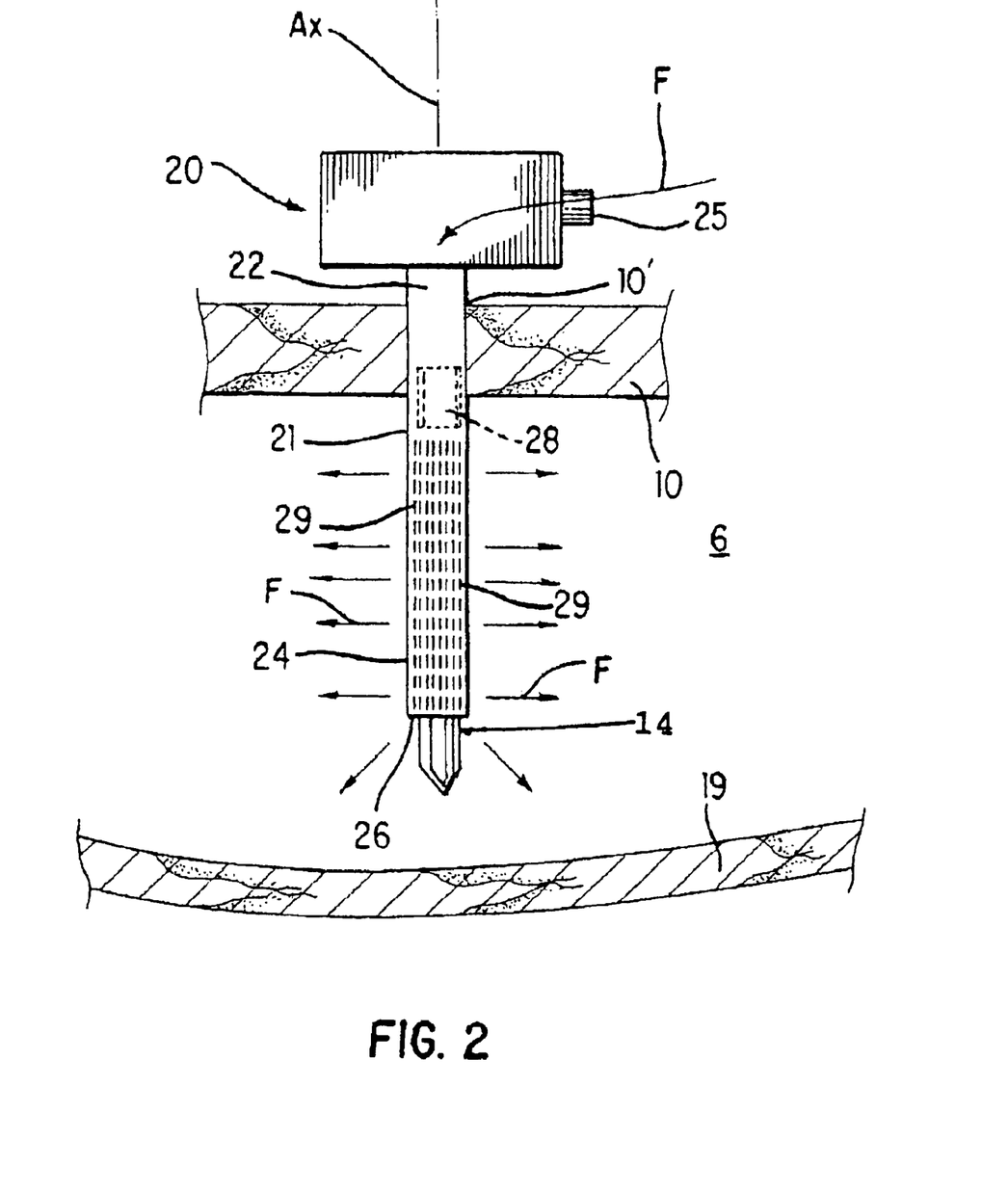
FIG. 2 is a side elevational view of a first embodiment of the trocar sleeve of this invention.
Figure 3:
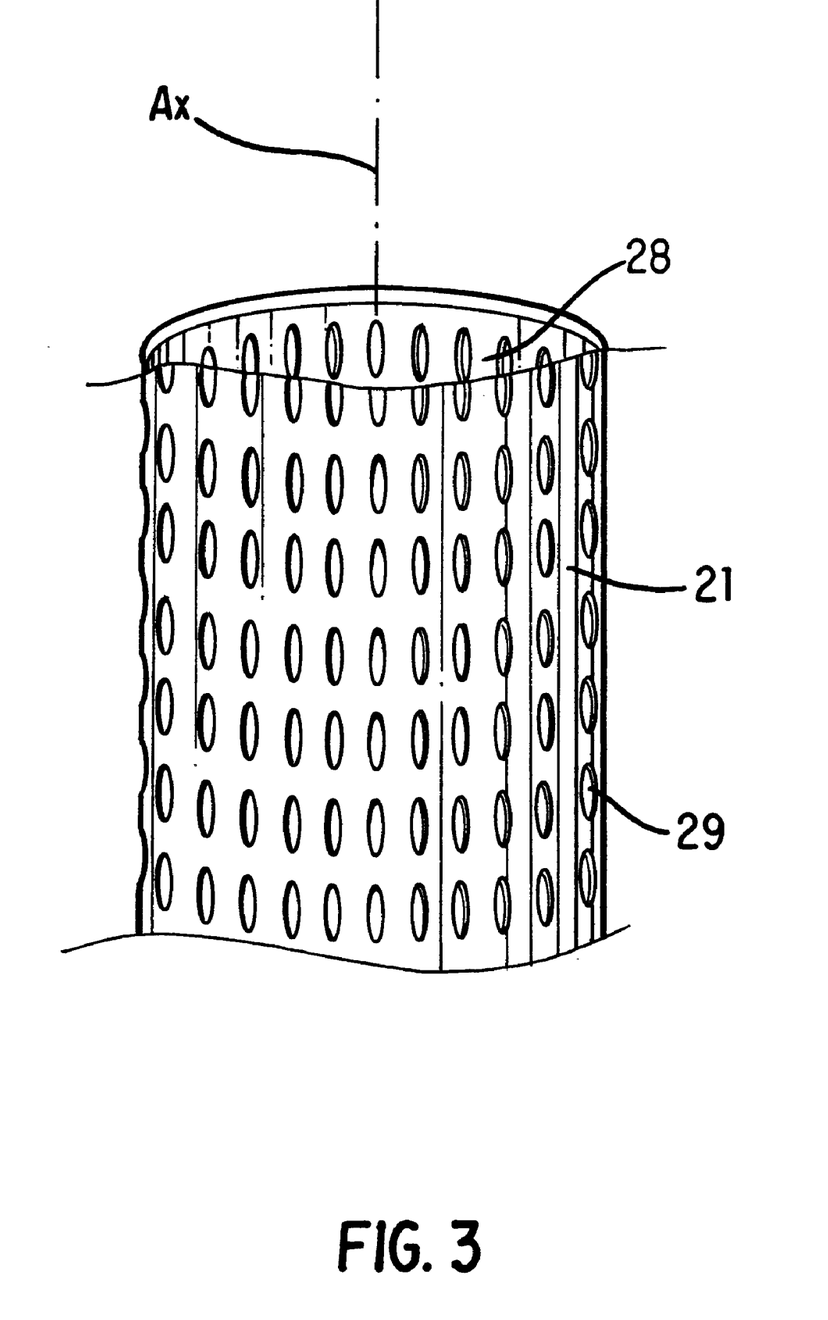
FIG. 3 is a partially cut away and enlarged view of a portion of the trocar sleeve of FIG. 2.

Referring now in detail to the drawings, in which like reference numerals indicate like parts throughout the several views, FIGS. 2 and 3 illustrate a first embodiment of a trocar sleeve of this invention. Referring now to FIG. 2, an elongate trocar sleeve 20 is shown. The trocar sleeve is formed as an elongate hollow tubular body member 21 about a central longitudinal axis, denoted by reference character "$A_x$". The body member has a proximal end of 22 and a spaced distal end 24. Formed at the proximal end of the body member is an inlet port 25, and an outlet port 26 is formed at the distal end of the body member. The inlet and outlet ports, respectively, in cooperation with the body member 21, define an elongate fluid flow conduit 28, also referred to as the lumen of the trocar sleeve, extending substantially along and within the length of the body member.

As shown in FIGS. 2 and 3, a plurality of spaced openings 29 are defined within the body member 21 and open inwardly to, i.e., they are in communication with, the conduit 28. The openings 29 begin at the distal end of the body member, and extend at least partially toward the proximal end of the body member, as desired. Although it is shown in FIG. 2 that the openings extend for approximately two-thirds of the length of the body member, the openings may extend the entire length if so desired, or may extend to only a desired length, based on the anticipated usage of the trocar sleeve in association with the anticipated thickness of the skin layer 10 of the person, or animal, into whose body the trocar sleeve has been passed. The openings 29 may be formed as either circular or round openings, as elongate or slotted openings, or of any desired size and shape for efficiently distributing the fluid passed through the trocar sleeve and into the body cavity 6.

As illustrated in FIG. 2, the method of inserting the trocar into the body cavity 6 of a person, or an animal, is accomplished by forming an opening 10' within the skin and tissue layers 10 of a person. The opening may be formed by any of the known methods, for example by using a Verres needle, a blind entry with a trocar, or the Hasson Open Method, all as desired or as required for the procedure being performed. The opening 10' is defined within the body such that it extends through the collective tissue layers 10, which include the subcutaneous tissue, fascia, muscle, and pre-pleural or pre-peritoneal areas for either the thoracic or abdominal cavities, respectively. A fluid, denoted by the reference character "F," is passed through the Verres needle or trocar sleeve for inflating the body cavity as the needle or trocar sleeve are passed therein.

Once the trocar assembly is passed through the opening 10' and into the body cavity 6, the obturator of the trocar is removed and the fluid "F" continues to flow into the trocar sleeve through the inlet port 25, into and through the conduit or the lumen 28, and exits the trocar sleeve at the outlet port 26 (FIG. 2). As shown in FIG. 1B, the lumen of the trocar sleeve will typically have at least one, and sometimes a plurality, of medical instruments 14 passed therethrough for use in the procedure being performed. The presence of these instruments in the lumen of the trocar sleeve greatly restricts the available cross-sectional area within the body member through which the fluid to be passed into the body may pass. It is this restriction of the effective cross-sectional area or diameter of the trocar sleeve available for fluid flow, by forcing the fluid to pass between the exterior surface(s) of the instrument(s) and the interior surface of the lumen, that leads to the creation of the undesired high pressure jetstream 18 (FIG. 1B). To eliminate this effect, therefore, and the resulting gas hyper-cooling of the surrounding tissues and organs within the body cavity adjacent the distal end of the trocar sleeve, and the localized and restricted circular delivery of the fluids or agents carried within the fluids within the body cavity, the trocar sleeve 20 provides the plurality of openings 29 extended in the lengthwise direction of the trocar sleeve.

Figure 8A:
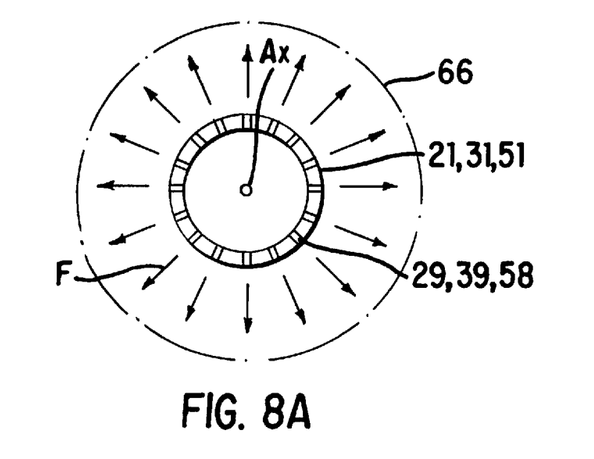
Figure 8B:
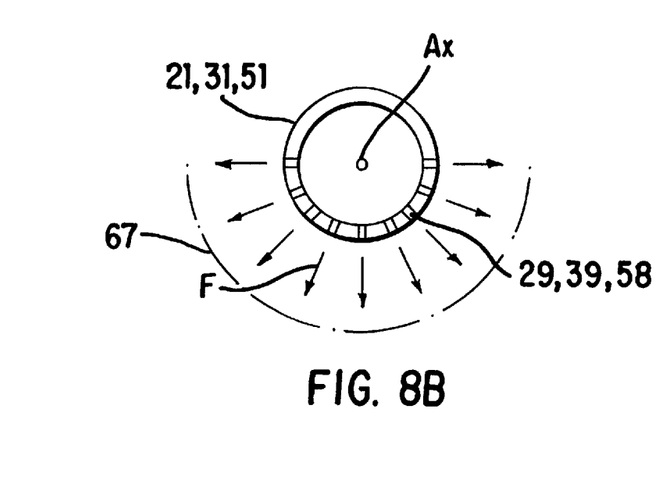

The effect of this construction is best shown in FIGS. 8A and 8B, which schematically illustrate the several embodiments 21 (FIG. 2), 31 (FIG. 4), and 51 (FIG. 6) of the trocar sleeve of this invention. Referring to FIG. 8A, a three hundred sixty degree radial pattern or fluid dispersion arc 66 is shown through which the fluid F passes from the openings 29 of the trocar sleeve in the area of the body cavity surrounding the trocar sleeve. This construction allows for the efficient and effective distribution of the fluid throughout the body cavity, and at a reduced pressure because of the plurality of openings 29 provided along the body member, rather than forcing the fluid to exit the body member only at its distal end.

When, for example, it is desired to avoid striking certain tissues, organs, or body structures within the body cavity adjacent the trocar sleeve such that a three hundred sixty degree dispersion arc may not be desirable, a one hundred eighty degree fluid dispersion arc 67 as shown in FIG. 8B may be used. Although not illustrated, it is anticipated that the fluid F may be passed through a radial arc of any desired radial degree based on the requirements of the procedure to be performed with which the trocar sleeve is used. Thus, and although not shown, it is anticipated that this radial arc could range anywhere from less than one degree to three hundred sixty degrees, all as desired.

Referring now to FIG. 3, the openings 29 are shown formed as elliptical openings extending parallel to the longitudinal axis $A_x$ of the body member, and are randomly spaced on the exterior surface of the body member/trocar sleeve. As described above, the openings 29 may be circular, if so desired, and may be regularly spaced (FIG. 5) or randomly spaced (FIG. 3), as desired.

Figure 4:
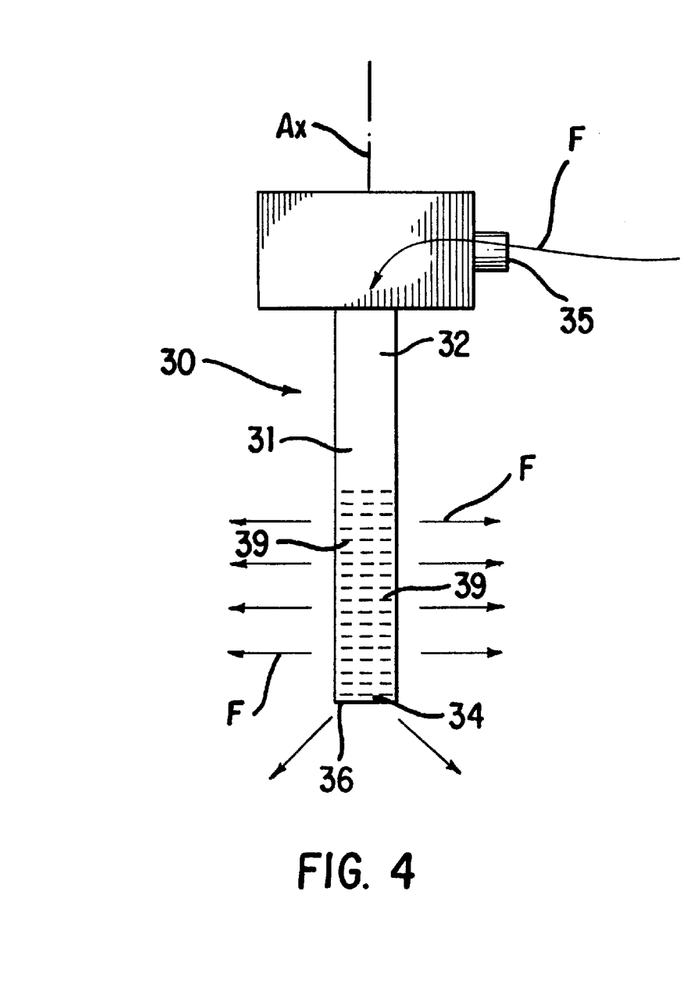
FIG. 4 is a side elevational view of a second embodiment of the trocar sleeve of this invention.
Figure 5:
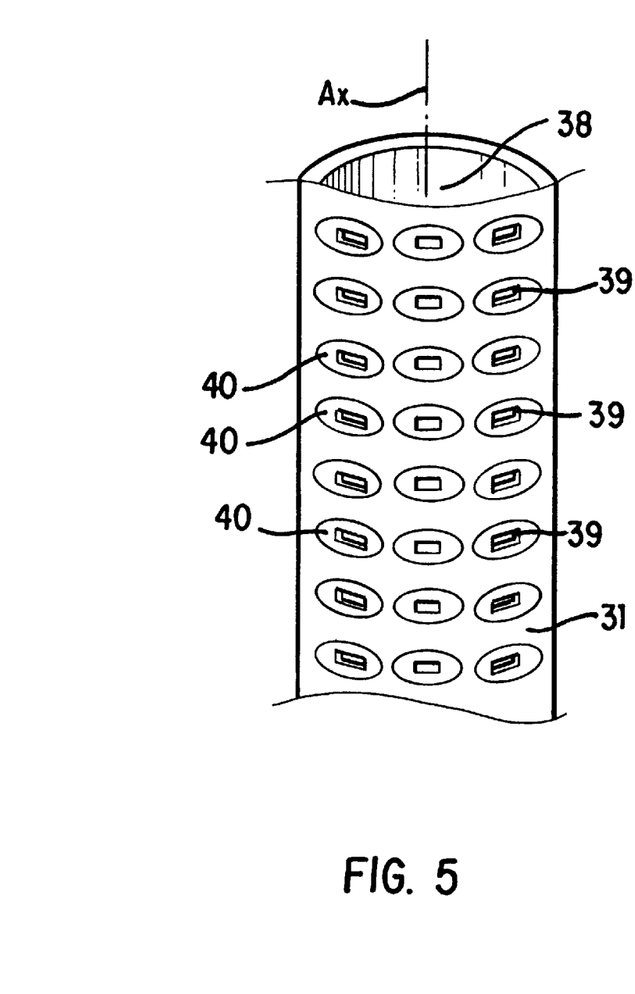
FIG. 5 is a partially cut away and enlarged view of a portion of the trocar sleeve of FIG. 4.

A second embodiment of the trocar sleeve 30 is illustrated in FIGS. 4 and 5. The trocar'sleeve 30 is formed once again as an elongate hollow tubular body member 31 about a central longitudinal axis $A_x$, and has a proximal end 32 and a spaced distal end 34. An inlet port 35 is defined at the proximal end of the body member, and an outlet port 36 is defined at the spaced distal end thereof. A fluid flow conduit 38 is defined within the tubular body member and extends from the inlet port 35 to the outlet port 36.

A spaced plurality of openings 39 are defined within the exterior surface of the body member 31, and extend through the body member into communication with the fluid flow conduit 38. Here, however, the openings 39 are formed within separate ones of a plurality of recessed dimples 40 defined within the exterior surface of the body member. Although one opening is shown in each recess 40, it is anticipated that any number of desired openings can be defined within the recesses, depending on the size and the number of the recesses so formed, and the size of the openings defined therein.

As best shown in FIG. 5, the openings 39 of the second embodiment of the trocar sleeve 30 are regularly spaced from one another on the exterior surface of the body member 31, and extend at least partially from the distal end 34 toward the proximal end 32 of the trocar sleeve. Again, the openings 39 may extend the entire length of the trocar sleeve if so desired, or for any desired length along the sleeve. It is anticipated, however, that although the respective openings 29 (FIG. 2), 39 (FIG. 4) and 59 (FIG. 6) of the trocar sleeves 21, 31, 51, respectively, may extend along the entirety of the length of the trocar sleeve if so desired, the openings will preferably be spaced from the proximal ends 22, 32, 52 thereof, respectively, such that there are no openings positioned adjacent the tissue layers 10 once the trocar sleeve has been passed therethrough in order to avoid damaging these tissue layers with the fluid passed through the body member.

Although the openings 39 shown in FIG. 5 are formed as elongate slots, these openings may be circular, or of any desired shape, which is true for any of the openings within any of the embodiments of the trocar sleeve of this invention. In FIG. 5 the openings 39 are shown as being formed perpendicularly with respect to the longitudinal axis of the body member, but could be formed to be parallel, or at an angle, with respect to the axis of the body member, as is also true for the respective openings 29, 59 in the other embodiments of the trocar sleeve disclosed herein.

Figure 6:
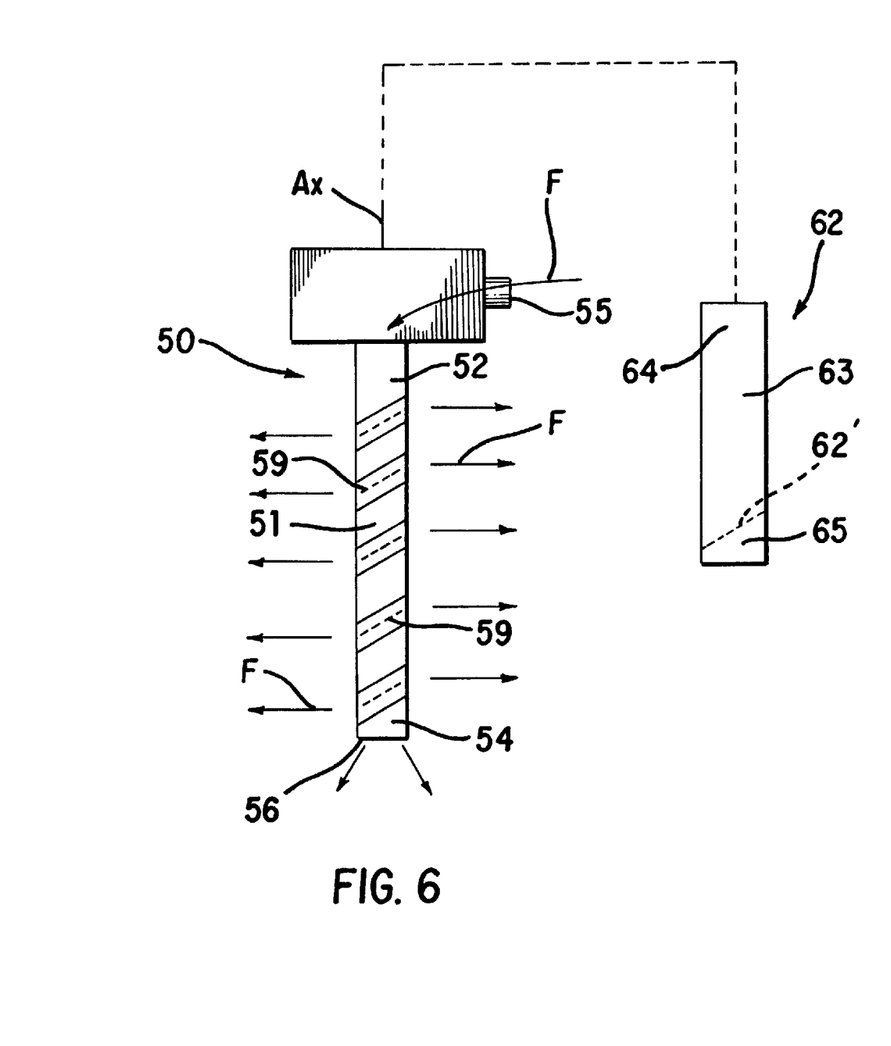
FIG. 6 is a side elevational view of a third embodiment of the trocar sleeve of this invention.
Figure 7:
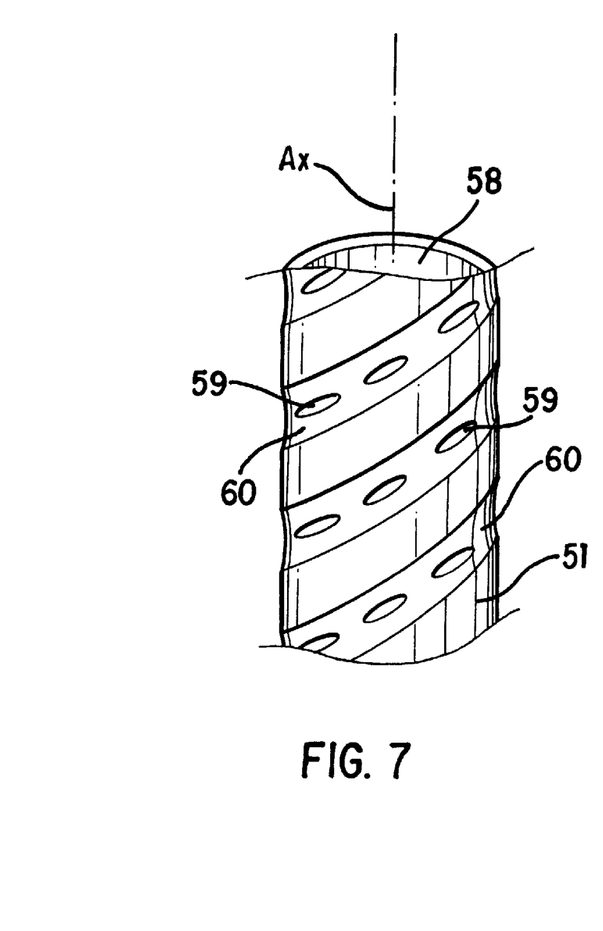
FIG. 7 is a partially cut away and enlarged view of a portion of the trocar sleeve of FIG. 6.

A third embodiment of the trocar sleeve 50 of this invention is illustrated in FIGS. 6 and 7. The trocar sleeve 50 has an elongate hollow tubular body member 51 formed about a central longitudinal axis $A_x$, with a proximal end 52 and a spaced distal end 54. An inlet port 55 is defined at the proximal end of the body member, and a spaced outlet port 56 is defined at the distal end thereof. The inlet and outlet ports, together with the body member, define a fluid flow conduit 58 extending for substantially the length of the body member, along and about the axis $A_x$.

A plurality of spaced openings 59 are defined within the exterior surface of the body member, and are in communication with the conduit 58. Here the openings 59 are defined within a continuous helical groove or recess 60 defined within the exterior surface of the body member, and extending from the distal end toward the proximal end thereof. The openings 59 are shown here as circles or elongate (elliptical) slots formed parallel to one another as they wind along the exterior surface of the body member, and are at an angle with respect to the longitudinal axis $A_x$. Although not illustrated, it is anticipated that rather than having a continuous helical groove or recess 60, that a series of spaced grooves or recesses could be formed parallel to one another within the exterior surface of the body member, and the openings 59 defined therein. Moreover, although the openings 59 are shown in FIG. 7 as being parallel to one another and at an angle to the axis $A_x$, it is possible that the openings, as with any of the embodiments of the trocar sleeve of this invention, can be formed to be parallel to the Axis $A_x$, (FIG. 3), perpendicular to the axis $A_x$ (FIG. 5), or at an angle to the axis $A_x$ (FIG. 7). Also, the openings 59 may take any desired shape, as described herein.

Referring to FIG. 6, an elongate tubular inner sheath 62 is shown for use with the trocar sleeve 50, and which may also be used with the other embodiments of the trocar sleeve 20, 30. The inner sheath 62 is sized and shaped to be passed through the proximal end of and into the body member of the trocar sleeve, and moved at least partially along the length of the trocar sleeve for selectively opening and closing selected ones of the openings 59 within the trocar sleeve 50 in FIG. 6, or the openings 29 for the trocar sleeve 20 in FIG. 2, or the openings 39 for the trocar sleeve 30 in FIG. 4.

The inner sheath 62 has an elongate body member 63 formed as an elongate hollow tubular body member so that once it is passed within the selected length of the trocar sleeve, the fluid is still permitted to pass therethrough, there being a suitable slot or channel (not illustrated) defined therein so that the fluid may pass from the inlet port of the body member into the conduit 58 thereof, and from there out through the openings 59 and into the body cavity 6 (FIG. 2). The body member 63 thus has a proximal end 64 and a spaced distal 65. Although not shown in FIG. 6, it is anticipated that the proximal end will be constructed to have a suitable grip thereat so that it can be grasped either by hand or by surgical instrument for being moved within the conduit 58 of the trocar sleeve 50. The inner sheath may also be formed as a helical or radially extending sheath 62', shown in broken line in FIG. 6.

Figure 8C:
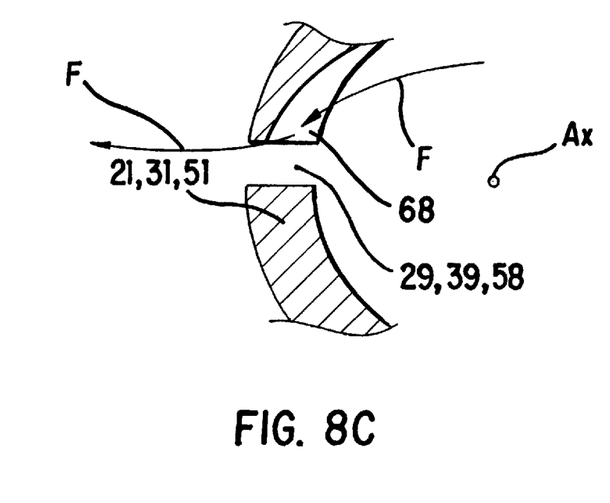
FIG. 8C is a fragmentary cross-sectional view of an illustrative fluid guide defined within the interior sidewall of a trocar sleeve of this invention.

Referring now to FIG. 8C, it is anticipated that a fluid guide or guides 68 may be defined within the interior surface of the respective conduits 28, 38, 58 of the several embodiments of the trocar sleeve for guiding the fluid F into a selected one or ones of the openings 29, 39, 58, respectively. Although the fluid guide 68 is shown in FIG. 8C as being defined in the side wall of the body member for a fluid opening, the fluid guide may also be formed as "rifling" defined in the interior surface of the body member in which a spaced series of helical grooves extend in the lengthwise direction of the body member. It is thus anticipated that separate ones of the fluid guide 68 can be provided for guiding the fluid to each opening, or selected openings, or for one or several selected series of the openings within the body member.

Referring now to FIGS. 2 through 7, it is anticipated that the openings 29, 39, and 59, respectively, will be sized in the range of from 0.01 millimeters to 5 millimeters in diameter, although other sized openings may be used as desired and as required to ensure the efficient distribution of the fluid passed into the body cavity. The respective openings may also vary in size as they extend along the length of the trocar sleeve, from either the distal or proximal ends thereof, respectively. Accordingly, the openings may increase in size from the distal toward the proximal end of the body member, or may decrease in size as they extend from the distal end toward the proximal end thereof, for varying, either increasing or decreasing, the pressure of the fluid delivered therethrough and into the body cavity, as desired.

Figure 9:
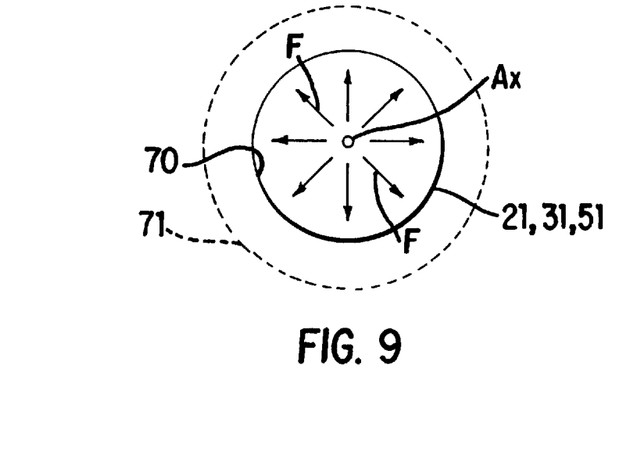
FIG. 9 is a top plan view of the trocar of this invention illustrating the radial expansion of the trocar sleeve as a fluid is passed therethrough.

Referring now to FIG. 9, another feature of the several embodiments of the trocar sleeve 21, 31, 51 of this invention is illustrated. Shown in solid lines in FIG. 9 is a first circumference 70 of the trocar sleeve as it is passed through the opening 10' defined in the tissue layers 10, and into the body cavity 6. When, however, fluid F is passed through the body member and into the body cavity, for example, the body member may be constructed of a resilient material such that it will radially expand about the longitudinal axis $A_x$, into the position shown by the second circumference 71, shown in broken line, so that the inner diameter of the trocar sleeve has increased. As this occurs, it is anticipated that respective openings 29, 39, 59 will also expand due to the expansion of the circumference or periphery of the tubular body member.

Each of the embodiments of the trocar sleeve 20, 30, 50 illustrated in FIGS. 2 through 9 may be formed of a rigid or a resilient plastic, from a metal, or of any desired material suitable for use as a trocar sleeve. For example, the trocar sleeve may be formed of a plastic-metal composite such that, for example, there may be a metal collar or ring at both the distal and proximal ends of the tubular body member, and the remainder of the body member is formed of a rigid or resilient plastic material. What is required is that the trocar sleeve, as well as the inner sheath 62 of this invention, be constructed of material approved by the United States Food and Drug Administration for use in surgical procedures, that the materials be durable, and capable of being sterilized completely for subsequent re-use. It is also anticipated, however, that the trocar sleeve may be constructed as a disposable one-time or throw-away device without the need for subsequent resterilization of the trocar sleeve.

Figure 10A:
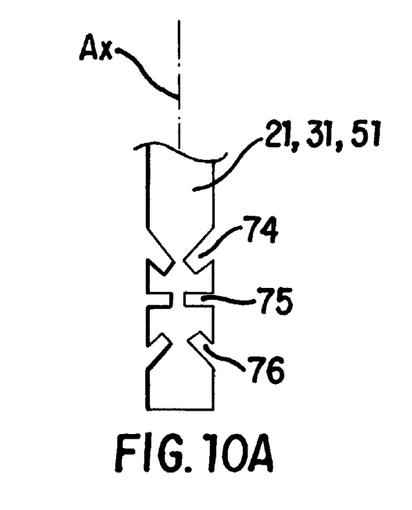
Figure 10B:
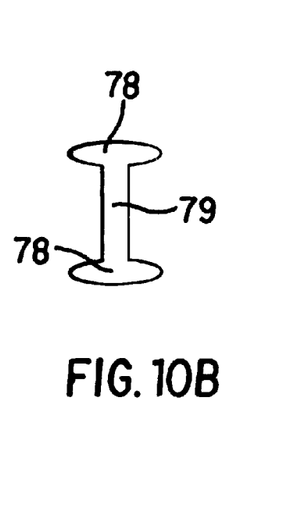
Figure 10C:
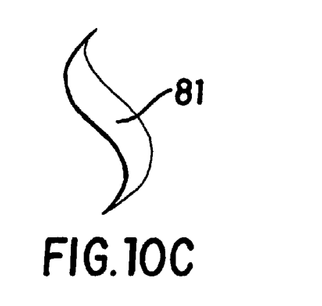

FIGS. 10A through 10C illustrate alternate types of the openings that may be defined within the body member of the several embodiments of the trocar sleeve of this invention. Referring first to FIG. 10A, a trocar sleeve 21, 31, 51 is shown extending about its central longitudinal axis $A_x$. Here, however, rather than using openings or slots defined in spaced series along the length of the trocar sleeve, a first pair of slots 74 are defined within the trocar sleeve and extend downwardly toward the distal end thereof, followed by a spaced second pair of slots 75 formed within circumference of the trocar sleeve, and then provided with a second pair of angled slots 76 defined therein and extending upwardly toward the proximal end of the body member.

In FIG. 10B, an opening that may be defined within any one of the respective body members of the trocar sleeve is illustrated, having a pair of spaced annular, elliptical or round, openings 78. These two openings are connected by a central elongate slotted opening 79. FIG. 10C illustrates an "S"-shaped opening 81 defined within the body member of the trocar sleeve. The several types of openings illustrated in FIGS. 10A–10C are intended to be illustrative, only, and do not limit the possible geometric design, size, or shape of the openings that may be defined within the body member/trocar sleeve.

Figure 11:
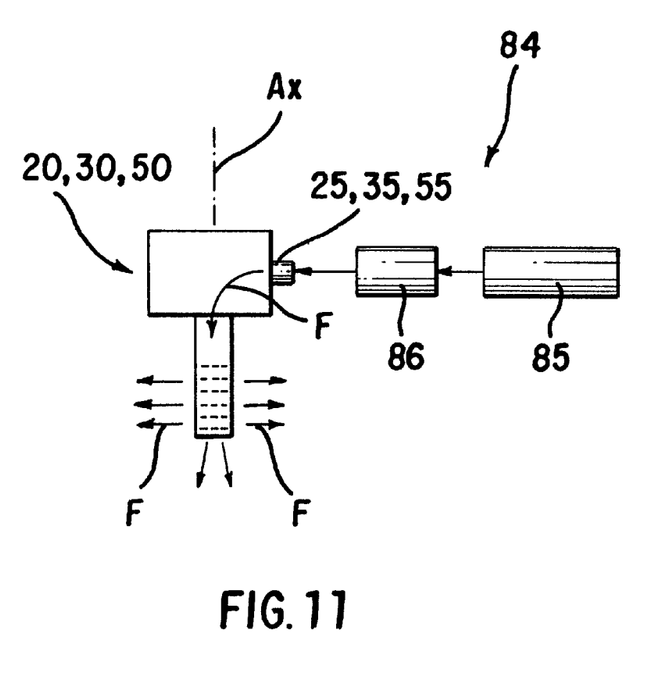
FIG. 11 is a schematic illustration of a system using the trocar of this invention.

FIG. 11 illustrates a system for use with the trocar sleeve of this invention. The system 84 includes a pressurized fluid supply 85, and a device 86 in communication with the pressurized fluid supply at the inlet port 25, 35, 55, respectively, of the several embodiments of the trocar sleeve described hereinabove. The pressurized fluid supply may be as simple as a cylinder of compressed gas, for example carbon dioxide or nitrous oxide, or may be a piped fluid delivery system having a remote fluid compressor station.

The fluid supply 85 may be any type of fluid, to include gases or liquids, now used or developed for future use in surgical procedures. The device 86 may be a stopcock or a leur lock, or may comprise a gas regulator if the fluid supply source 85 is not otherwise pressure regulated. It is also anticipated that the fluid supply may be delivered from a syringe passing the fluid into the trocar sleeve, an intravenous bag, a bulb pressure manometer, or any other known device capable of transferring a fluid, either a liquid or a gas, from a supply of the fluid to the trocar sleeve. The fluid may thus be a gas stream, an intravenous stream, a liquid atomized within a gas.

All that is necessary is that the fluid be capable of being introduced into the trocar sleeve to attain the benefits of this design, system and method of usage. The fluid may thus be added to the trocar sleeve separate and apart from the insufflating fluid passed into the trocar sleeve through an insufflator, a pressurized fluid source and/or supply, used to distend the body cavity, where the second fluid to be administered to the body cavity is merely placed or passed into the trocar sleeve and allowed to flow toward the distal end thereof positioned in the body cavity, and radially dispersed therefrom by the insufflating fluid in an efficient manner, namely being dispersed from the trocar sleeve radially and at a reduced pressure compared to the known types of trocar devices and methods of use.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein, and that many modifications and other embodiments of the invention are intended to be included within the scope of the appended claims. Moreover, although specific terms are employed herein, as well as in the claims, they are used in the generic and descriptive sense only, and not for the purposes of limiting the described invention, nor the claims which follow.

I claim:

1. A method of delivering a pressurized fluid stream carrying one or more agents under pressure into a body, said method comprising the steps of:
   a) inserting a distal end of an elongate trocar sleeve into the body, the trocar sleeve having a proximal end spaced from its distal end;
   b) passing the fluid to be delivered into the proximal end of the trocar sleeve and flowing the fluid through an open chamber in the trocar sleeve, the open chamber being partially obstructed when housing an instrument therein to produce a partially obstructed cross sectional fluid flow area through the open chamber; and
   c) discharging the fluid from the trocar sleeve into the body at a velocity below a jet streaming velocity.

2. A device for insertion into a body for use in delivering a pressurized fluid stream carrying one or more agents under pressure into the body, said device comprising:
   an elongate tubular body member formed about a longitudinal axis;
   said body member having a proximal end and a spaced distal end;
   an inlet port defined at the proximal end of the body member;
   an outlet port defined at the distal end of the body member;
   the inlet port and the outlet port defining in cooperation with the body member a conduit having an open fluid chamber extending substantially the length of the body member, said open fluid chamber at times partially obstructed by an instrument to produce an obstructed cross sectional fluid flow area through the open fluid chamber and thereby increase a velocity of a fluid stream flowing therein to a jet streaming condition; and
   a plurality of spaced openings defined in the body member and opening into at least a portion of the obstructed cross sectional fluid flow area in said conduit, said plurality of openings each having a cross sectional fluid discharge area and each having a fluid stream discharging into a body cavity with the total fluid cross sectional fluid discharge area of said plurality of openings larger than the obstructed cross sectional fluid flow area to thereby maintain a velocity of the fluid stream discharging from each of the plurality of openings in a non jet streaming condition.

3. The device of claim 2, said plurality of spaced openings being randomly spaced from one another.

4. The device of claim 1, said plurality of spaced openings being regularly spaced from one another.

5. The device of claim 1, said body member being formed as an elongate rigid tubular body member about said longitudinal axis.

6. The device of claim 1, further comprising a spaced plurality of dimples defined in the exterior surface of the body member and extending from the distal end of the body member, at least partially toward the proximal end thereof, said plurality of spacea openings being defined within said dimples.

7. The device of claim 2, further comprising a continuous helical groove defined within the exterior surface of the body member land extending from the distal end of the body member at least partially toward the proximal end thereof, said plurality of spaced openings being defined within said helical groove.

8. The device of claim 2, said pre-determined radial arc comprising an arc of approximately one hundred-eighty degrees.

9. The device of claim 1, said pre-determined radial arc comprising an arc of approximately three hundred-sixty degrees.

10. The device of claim 1, each opening of said plurality of openings is sized in the range of from approximately 0.01 millimeters to approximately 5 millimeters.

11. The device of claim 2 wherein the openings of said plurality of openings vary in size as they extend/along the length of the body member.

12. The device of claim 1, said plurality of openings being spaced from the proximal end of the body member.

13. The device of claim 1, wherein the openings of said plurality of openings are formed as elongate openings in the body member.

14. The device of claim 13, wherein the openings of said plurality of openings are formed to be parallel to the axis of the body member.

15. The device of claim 13, wherein the openings of said plurality of openings are formed to be perpendicular to the axis of the body member.

16. The device of claim 13, wherein the openings of said plurality of openings are formed parallel to one another and at an angle with respect to the axis of the body member.

17. The device of claim 2, further comprising an elongate tubular inner sheath member constructed and arranged to slide within the conduit of the body member, and at least partially along the length thereof.

18. The device of claim 17, said sheath member being sized and shaped to cover at least some of the openings of said plurality of openings in the body member.

19. The device of claim 2, said body member being constructed and arranged to expand radically about its longitudinal axis as the fluid to be delivered into the body is passed therethrough.

20. The device of claim 2, further comprising at least one fluid guide defined within the surface of the conduit and extending outwardly of the axis of the body member, said at least one guide being constructed and arranged to guide the fluid to be delivered into the body to at least one of the plurality of openings defined in the body member.

21. A system for delivering a pressurized fluid stream carrying one or more agents under pressure into a body, said system comprising:
  a) a trocar sleeve, comprising:
    i) an elongate tubular body member formed about a longitudinal axis;
    ii) said body member having a proximal end with an inlet port defined thereat, and a spaced distal end with an outlet port defined thereat;
    iii) an open chamber conduit defined within the body member by the inlet port and the outlet port in cooperation with the body member, said conduit extending substantially the length of the body member said open fluid chamber at times partially obstructed by an instrument to produce a partially obstructed cross sectional fluid flow area through the open fluid chamber and thereby increase a velocity of a fluid stream flowing therein; and
    iv) a plurality of spaced openings defined in the body member and opening into at least a portion of the obstructed cross sectional fluid flow area in said conduit, said plurality of openings each having a cross sectional fluid discharge area and each having a fluid stream discharging into a body cavity with the total fluid cross sectional fluid discharge area of said plurality of openings larger than the obstructed cross sectional fluid flow area so as to maintain a velocity of the fluid stream discharging from each of the plurality of openings in a non jet streaming condition;
  b) a supply of the fluid to be passed into the body; and
  c) a means for introducing the fluid into said body member.

22. The device of claim 21, said means for introducing the fluid comprising a stopcock, a leur lock, a pressure regulator device, a syringe, an intravenous bag, and a bulb pressure manometer.

23. A method of delivering a pressurized fluid stream carrying one or more agents under pressure into a body, said method comprising the steps of:
  a) inserting a distal end of an elongate trocar sleeve into the body, the trocar sleeve having a proximal end spaced from its distal end;
  b) passing the fluid to be delivered into the proximal end of the trocar sleeve and flowing the fluid through an open chamber in the trocar sleeve, the open chamber being partially obstructed when housing an instrument therein to produce a partially obstructed cross sectional fluid flow area through the open chamber to thereby increase a velocity of a fluid stream flowing therein; and
  c) dispersing the fluid from the trocar sleeve and into the body through a plurality of spaced openings defined in the trocar sleeve with the plurality of openings each having a cross sectional fluid discharge area discharging a fluid stream into the body with the total fluid cross sectional fluid discharge area of said plurality of openings larger than the partially obstructed cross sectional fluid flow area so as to maintain a velocity of the fluid stream discharging from each of the plurality of openings in a non jet streaming condition.

24. The method of claim 23, step c) comprising the step of dispersing the fluid from the trocar sleeve through said plurality of spaced openings in a lengthwise direction of the trocar sleeve extending from the distal end thereof at least partially toward the proximal end thereof.

25. The method of claim 23, step c) comprising the step of dispersing the fluid from the trocar sleeve through said plurality of spaced openings substantially along the length of that portion of the trocar sleeve inserted into the body.

26. A trocar sleeve for insertion into a body for use in carrying viewing or surgical instruments while continuing to deliver a fluid stream carrying one or more agents into the body, said trocar sleeve comprising:
  an elongate tubular body member formed about a longitudinal axis;
  said body member having a proximal end and a spaced distal end;
  an inlet port defined at the proximal end of the body member;
  the inlet port and the outlet port defining in cooperation with the body member a conduit having an open fluid chamber extending substantially the length of the body member, said open fluid chamber at times partially obstructed by an instrument to produce an obstructed cross sectional fluid flow area through the open fluid chamber and thereby increase a velocity of a fluid stream flowing therein to a jet streaming condition; and
  a plurality of spaced openings defined in the body member and opening into the obstructed cross sectional fluid flow area in said conduit, said plurality of openings each having a cross sectional fluid discharge area and each having a fluid stream discharging into a body cavity with the total fluid cross sectional fluid discharge area of said plurality of openings larger than the obstructed cross sectional fluid flow area to thereby maintain a velocity of the fluid stream discharging from each of the plurality of openings in a non jet streaming condition.

* * * * *